United States Patent
Berger et al.

(10) Patent No.: US 11,599,191 B2
(45) Date of Patent: Mar. 7, 2023

(54) AUTOMATIC LOCALIZATION OF A STRUCTURE

(71) Applicant: Siemens Healthcare GmbH, Erlangen (DE)

(72) Inventors: Martin Berger, Erlangen (DE); Anton Nekovar, Neunkirchen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/940,916

(22) Filed: Jul. 28, 2020

(65) Prior Publication Data
US 2021/0034148 A1    Feb. 4, 2021

(51) Int. Cl.
*G06F 3/01*    (2006.01)

(52) U.S. Cl.
CPC .................... *G06F 3/013* (2013.01)

(58) Field of Classification Search
CPC ................ G06F 3/013; G06F 3/011
See application file for complete search history.

(56) References Cited

U.S. PATENT DOCUMENTS

2018/0268552 A1    9/2018 Wood et al.
2019/0354177 A1*  11/2019 Horiuchi ............. G06F 3/167

OTHER PUBLICATIONS

German Office Action for related German Application No. 102019211536.5, dated Jul. 7, 2020.
Spampinato, Concetto et al., "Using the Eyes to 'See' the Objects," Proceedings of the 23rd ACM international conference on Multimedia, pp. 1231-1234, Oct. 2015.
Kang, Dongwoo, et al. "Feasibility of Eye-tracking based Glasses-free 3D Autostereoscopic Display Systems for Medical 3D Images." BioImaging. 2016. pp. 134-138.
Lanzer, Peter, et al. "Eye tracking in catheter-based cardiovascular interventions: Early results." Journal of Medical Imaging 4.3 (2017): 035502-035502-8.

* cited by examiner

*Primary Examiner* — Nelson M Rosario
*Assistant Examiner* — Scott D Au
(74) *Attorney, Agent, or Firm* — Lempia Summerfield Katz LLC

(57) ABSTRACT

According to a computer-implemented method for the automatic localization of a structure, an individual image which maps an object with the structure is displayed on a display surface. A gaze movement of a user is captured by a gaze capture system and, on the basis thereof, a gaze capture signal is generated. By a computer unit, dependent upon the gaze capture signal, at least one image point of the individual image is identified, which at least partially maps the structure.

14 Claims, 2 Drawing Sheets

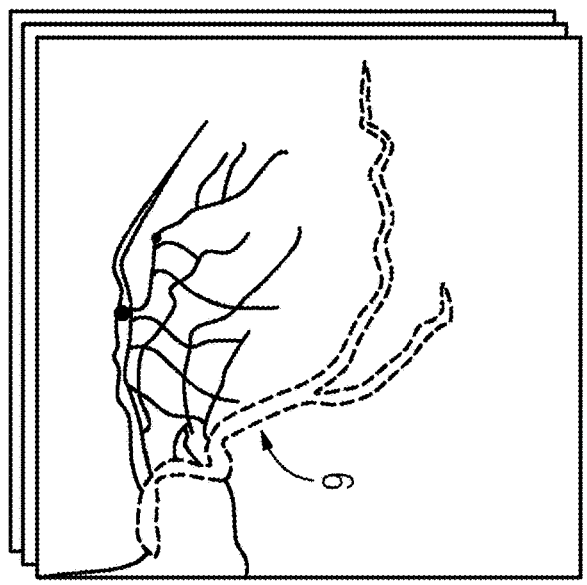
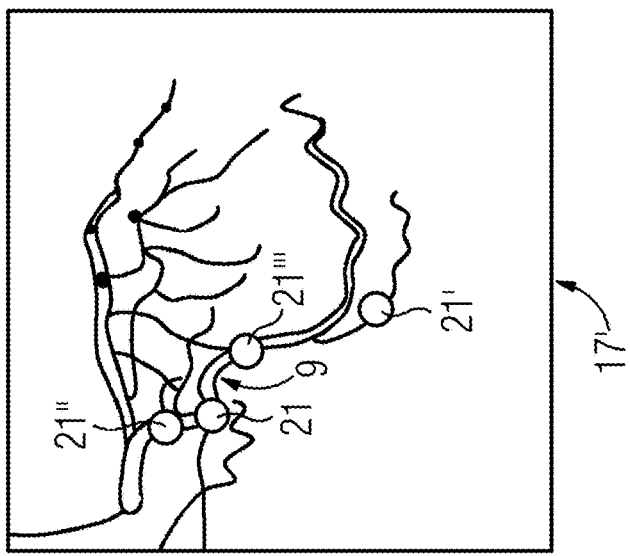
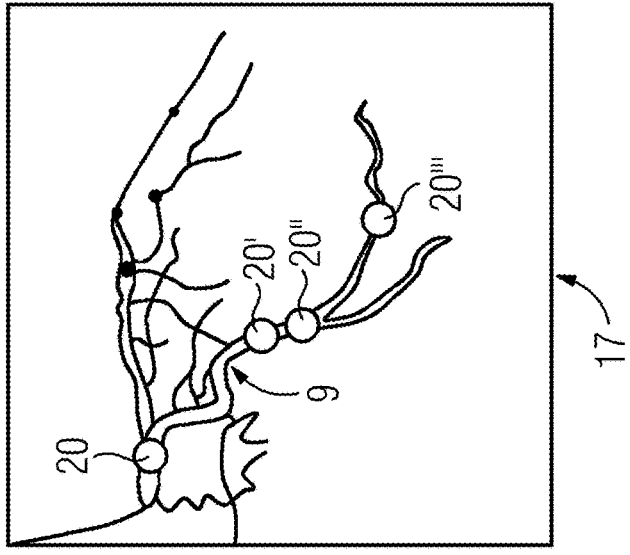

AUTOMATIC LOCALIZATION OF A STRUCTURE

The present patent document claims the benefit of German Patent Application No. 10 2019 211 536.5, filed Aug. 1, 2019, which is hereby incorporated by reference.

TECHNICAL FIELD

The present disclosure relates to a computer-implemented method for the automatic localization of a structure, wherein an individual image which maps an object with the structure is displayed on a display surface. The disclosure further relates to an apparatus for the automatic localization of a structure, a computer-implemented method for training a software module, and a computer program.

BACKGROUND

In different applications in which an object is analyzed or manipulated by a person with the support of imaging, (e.g., in the field of medical applications), the correct determination of a position of a structure in the image data is of decisive significance for further method acts. In the medical context, this is the case, for example, for analytical or diagnostic methods or for interventions that are supported by imaging methods, (e.g., fluorescence-based methods). In particular, for many medical uses, a correct segmentation of an anatomical object is decisive for further treatment or analytical acts.

Existing segmentation methods and other methods for structure localization in image data require user input or the selection of image points or image regions by the user in order to be able to provide adequate results. For example, the user may manually place seed points, which may be designated initial points for segmentation and lie within the anatomical structure of interest or which draw approximate outlines round the structure.

The manual interaction of the user with the localization system or the segmentation algorithm is disadvantageous because the interaction interrupts the operational processes of the user, deflects the user thereby, and also takes up a corresponding amount of time. These interactions also require a physical operation of an input device by the user, which is disadvantageous particularly in sterile environments.

SUMMARY AND DESCRIPTION

It is therefore an object of the present disclosure to provide an improved concept for the automatic localization of a structure in images, which enables a higher degree of automation and reduces manual acts for the localization of the structure.

The scope of the present disclosure is defined solely by the appended claims and is not affected to any degree by the statements within this summary. The present embodiments may obviate one or more of the drawbacks or limitations in the related art.

The improved concept is based upon the idea of capturing a gaze movement of a user by a gaze capture system and identifying at least one image point which relates to the structure, dependent upon the captured gaze movement, in particular, of identifying it automatically.

According to an aspect of the improved concept, a computer-implemented method for the automatic localization of a structure is provided. Thereby, an individual image which maps an object having the structure is displayed on a display surface, (e.g., of a display device), in particular, by a computer unit. A gaze movement of a user, (e.g., of a user of an imaging apparatus or an apparatus for the automatic localization of a structure), is captured by a gaze capture system, in particular, while the individual image is displayed on the display surface. Based on the captured gaze movement, a gaze capture signal is generated, in particular, by the gaze capture system. By the computer unit, dependent upon the gaze capture signal, at least one image point of the individual image is identified, (e.g., automatically identified), wherein the at least one image point at least partially maps the structure.

The localization of the structure may refer to the determination of a position of the structure or of a part of the structure.

The object may be a part of a human or animal body, (e.g., one or more organs or other anatomical objects), or a part of a plant. The object may also be an inanimate object.

The structure may be a region of interest of the object, that is, a region which is relevant for an analysis, treatment, or manipulation of the object. For example, the structure may be a point or region of the object. In the medical context, the structure may be an anatomical structure or a part of an anatomical object. The structure may be an organ, an anatomical vessel, a tumor, or respectively, a part thereof. The expression tumor may be interpreted broadly, so that apart from neoplasms in body tissues, other masses in tissues, cysts, or the like may also be included thereby.

The individual image relates, in particular, to the representation of a corresponding image data set which contains, for example, at least gray values of its individual image points and associated positions of the individual image points.

The individual image may be a two-dimensional mapping of the object or a two-dimensional part of a three-dimensional representation of the object.

The at least one image point may be a set of image points, (e.g., a coherent set of image points).

The image data set may be present in a stored form. In order to display the individual image on the display surface of the display device, the computer unit may access the stored image data set. The computer unit or the display device may receive the image data set from the imaging apparatus for display of the image data set, including in real time.

That the at least one image point at least partially maps the structure may be understood to mean that a complete mapping of the structure contains the at least one image point. In other words, the structure is represented in the individual image by a plurality of image points which contains the at least one image point.

The identification of the at least one image point includes, in particular, the determination of the position of the at least one image point, in particular, each image point of the at least one image point in the individual image, (e.g., the localization of the at least one image point).

In other words, it is determined, based on the improved concept, which image points of the individual image correspond to the gaze movement of the user or to a gaze position defined by the gaze movement on the display surface. Through the allocation to the at least one image point, this goes beyond the mere determination of the gaze position on the display surface and, where relevant, beyond a following of the gaze position.

With the improved concept, use is made of the fact that the user of the apparatus may distinguish relevant from less relevant image regions, based on relevant experience or expertise, with a high level of accuracy and reliability. Accordingly, the user's gaze moves to positions of the display surface that belong to the structure. Particularly in the case of physicians or other medical personnel, therefore, the expert knowledge that is present and is effectively "stored" in the form of the gaze movement of the user is thus utilized in order, without further manual interaction of the user with the system, to identify the at least one image point.

The localization or a possible subsequent automatic segmentation of the structure is thus entirely or partially automated and manual interactions of the user with the system are reduced, so that the operational processes of the user need not be interrupted, for example, in order to place or define seed points or an approximate outline of the structure manually. The operation of an input device such as a computer mouse or a keyboard which is thus omitted is advantageous, in particular, in sterile environments.

According to the improved concept, the experience of the user may therefore be used efficiently without this needing to be explicitly formulated based on rules, work instructions, or the like.

The identified at least one image point may be used by the computer unit for segmentation, (e.g., anatomical segmentation), of the structure.

In different embodiments, the at least one image point identified may be used by the computer unit for localization of a characteristic or relevant position in the object, that is, for localization of so-called landmarks in the mapping.

According to at least one embodiment of the computer-implemented method for automatic localization of a structure according to the improved concept, a gaze position on the display surface is determined by the computer unit, dependent upon the gaze capture signal. The at least one image point may be determined by the computer unit based on the gaze position.

In other words, based on the gaze movement of the user, it is determined which point or which region of the display surface the user is looking at or which region on the display surface the user is focusing on. Because the gaze position is allocated to the at least one image point, the at least one image point is determined dependent upon the gaze position.

Because the at least one image point corresponds to the gaze position of the user, it may be assumed that the at least one image point represents a region of heightened interest for the user, so that it may be used for localization of the structure and, for example, for segmentation of the structure.

For example, the use of the image region corresponding to the gaze position as a seed point for the segmentation may replace a manual input of a seed point by the user.

According to at least one embodiment, an image sequence which contains the individual image and at least one further individual image may be displayed on the display surface, in particular, by the computer unit. The gaze movement of the user is captured, in particular, by the gaze capture system during the display of the image sequence, (e.g., continuously). The gaze capture signal is generated based on the gaze movement of the user captured during the display of the image sequence, in particular, by the gaze capture system.

In order to display the image sequence on the display surface, individual images, (e.g., the individual image and the at least one further individual image) may be displayed successively and, if relevant, periodically repeating, wherein each individual image or further individual image is displayed for a pre-determined display duration.

That the gaze movement of the user is captured during the display of the image sequence may be understood to mean that the gaze movement is captured during the display of the individual image and during the display of each of the further individual images.

In different embodiments, the individual image and the at least one further individual image form a plurality of at least two individual images, at least five individual images, at least ten individual images, or at least 30 individual images.

The display of the image sequence permits, by the dynamic representation of the object or of the structure, more information or a greater information density to be provided on the display surface, for example, a movement of the object or the structure. In the medical context, for example, a blood flow may also be visualized by the image sequence.

Due to the greater information density that is provided to the user, the user may recognize the structure with a high level of reliability or accuracy. Accordingly, the evaluation of the gaze capture signal or the gaze movements is also more reliable or more accurate. Consequently, a more accurate localization of the structure and, if relevant, a more accurate segmentation of the structure is enabled.

According to at least one embodiment of the method, in particular, by the computer unit, dependent upon the gaze capture signal, at least one further image point is identified for each further individual image of the at least one further individual image, wherein the respective at least one further image point at least partially maps the structure.

Thereby, the at least one further image point may correspond to the at least one image point of the individual image or may be located at another site of the structure.

According to at least one embodiment, dependent upon the gaze capture signal, in particular, by the computer unit, for each further individual image, a respective further gaze position on the display surface is determined. The respective at least one further image point is determined based on the respective further gaze position.

According to at least one embodiment, a position of the identified at least one image point and possibly a respective position of each of the at least one further image point is stored on a storage medium, in particular, by the computer unit and, in particular, dependent upon the gaze capture signal.

According to at least one embodiment, the display of the image sequence is repeated at least once, in particular, multiple times, (e.g., periodically). The gaze movement is captured by the gaze capture system during a plurality, that is, during at least two or all, of the repetitions and the gaze capture signal is generated based on the gaze movement captured during the plurality of repetitions.

By the possible plurality of repetitions, the position of the image point or the gaze position of the user may be verified and/or additional gaze positions may be determined for the individual image or the further individual images. Accordingly, the at least one image point or the respective at least one further image point can be determined with greater accuracy and reliability.

According to at least one embodiment, the display of the image sequence is paused, for example, by the computer unit. During the pausing, the individual image or one of the further individual images is displayed, in particular, statically. The gaze movement is captured by the gaze capture system during the pausing and the gaze capture signal is generated based on the gaze movement captured during the pausing.

The pausing may be initiated automatically or by a user input.

The pausing may therefore take place for a pre-determined duration or may be ended by a further user input.

By the pausing and the correspondingly longer duration for which the user may look at the corresponding individual image, for each individual image, additional gaze positions and corresponding image points which map the structure may be captured or determined. The number of repetitions of the image sequence required may thus be reduced and/or the localization of the structure may take place more accurately.

According to at least one embodiment, the object is mapped by an imaging apparatus in order to generate the individual image and possibly the at least one further individual image.

The imaging apparatus may be an X-ray device, a computed tomography device, a magnetic resonance tomography device, a device for radionuclear irradiation, or an ultrasonic device.

In particular, the imaging apparatus is an apparatus with which a time-resolved or time-dependent mapping of the object is possible.

According to at least one embodiment, at least one gaze movement of at least one further user is acquired by the gaze capture system and, based on the captured at least one further gaze movement, at least one further gaze capture signal is generated by the gaze capture system. The at least one image point is identified by the computer unit from the gaze capture signal and the further gaze capture signal.

In such embodiments, not only the experience of the user who, for example, carries out the analysis or manipulation of the object, but also that of the further users who, for example, assist the user, may be used to localize the structure. Thus, a further increased accuracy or reliability of the localization or the segmentation may be achieved.

The gaze capture system may contain an individual gaze capture system for the user and for each of the further users. For example, the individual gaze capture systems may each be configured as devices mountable on the head which the respective user may wear similarly to a pair of glasses.

According to at least one embodiment, the structure is segmented at least partially automatically by the computer unit based on the at least one image point and possibly based on the at least one further image point.

The segmentation of the structure may be understood to mean that all the relevant image regions in the individual image or in the at least one further individual image which belong to the structure are identified. In particular, the structure as a region of interest is thereby separated from less relevant regions, for example, surrounding regions which surround the structure.

The fact that the segmentation takes place at least partially automatically may be understood to mean that by the computer unit, regions of the structure are identified automatically dependent upon the at least one image point or the at least one further image point which themselves do not correspond to the at least one image point or the at least one further image point. A manual input by the user may be possible for confirmation, correction, or enhancement of the segmentation, but such manual input is not required.

For example, the at least one image point and/or the at least one further image point may be used as respective seed points for the segmentation. The segmentation may be carried out by the computer unit based on classical image processing methods, for example, methods for edge recognition, for contrast analysis or for gray scale analysis, or based on an algorithm that has been trained by machine learning.

According to at least one embodiment, the structure is visually emphasized in the individual image or the image sequence on the display surface, in particular, by the computer unit.

According to a further independent aspect of the improved concept, a method for automatic segmentation of an anatomical structure is provided. Thereby, an individual image which maps an object having the structure is displayed on a display surface, a gaze movement of a user is captured by a gaze capture system and, on the basis thereof, a gaze capture signal is generated. By a computer unit, dependent upon the gaze capture signal, at least one image point of the individual image is identified, wherein the at least one image point at least partially maps the structure. The structure is segmented at least partially automatically by the computer unit based on the at least one image point.

Further embodiments of the method for automatic segmentation of an anatomical structure follow directly from the different embodiments of the method for the automatic localization of a structure.

According to a further independent aspect of the improved concept, a computer-implemented method for training a software module for machine learning, in particular a software module which contains a computer program or software for machine learning, is provided. Thereby, a training image which maps a training object with a training structure is displayed on a display surface, (e.g., of a display device), for example, by a training computer unit. A gaze movement of a user is captured by a gaze capture system and based on the captured gaze movement, a training signal is generated, (e.g., by the training computer unit). The training structure is segmented at least partially automatically by a training computer unit based on the training signal. The software module is trained based on a result of the segmentation by the training computer unit.

The software module is, in particular, a source code which is stored on a computer-readable storage medium, or a compilation of a plurality of source codes. The training computer unit may access the software module in order to carry out the corresponding source code or the compilation of the source codes. The training computer unit may also access the computer-readable storage medium by writing, e.g., in order to adapt the software module to train the software module, in particular to adapt or amend parameters of the software module.

As software or a computer program for machine learning or an item of software or a computer program may be understood to be based on, or may be trained based on, a method for machine learning.

The software module for machine learning may be configured as an automatic classifier, as an artificial neural network (e.g., as a convolutional artificial neural network), as a software module for reinforcement learning, as a software module for cluster analysis, as a support vector machine, or the like.

The training of the software module by the training computer unit includes, in particular, the adaptation of one or more parameters of the software module or of the source code stored thereon, dependent upon the result of the segmentation. In the case of a neural network, the training includes, in particular, the adaptation of the corresponding weights of the neural network dependent upon the result of the segmentation.

According to at least one embodiment, the training of the software module includes the comparison of the result of the segmentation with a reference result, that is for example, a pre-determined reference segmentation of the structure.

Alternatively, or additionally, the training of the software module may also include a verification or falsification of the automatic segmentation by a user input.

According to at least one embodiment, the computer-implemented method for training the software module is carried out during a computer-implemented method for automatic localization of a structure according to the improved concept or as part of such a method.

The training or the method for training the software module may thus be used in real time during an operative use of the software module in a method for the automatic localization according to the improved concept. Thereby, in particular, the computer unit may use the software module in operative use for segmentation of the structure.

The training computer system may be the computer unit or a further computer unit.

In different embodiments of the method for training the software module, the individual image of a method for the automatic localization of a structure is used as a training individual image. The training object then corresponds to the object, the reference structure corresponds to the structure, and the training signal corresponds to the gaze capture signal.

According to at least one embodiment, by the training computer unit, dependent upon the training signal, at least one image point of the training individual image is identified, wherein the at least one image point of the training individual image at least partially maps the training structure. The training structure is segmented at least partially automatically by the training computer unit based on the at least one image point.

According to at least one embodiment of the computer-implemented method for the automatic localization of a structure, the structure is segmented at least partially automatically by a software module for machine learning, in particular, by the computer unit, wherein the software module is or has been trained based on a computer-implemented method for training a software module for machine learning according to the improved concept.

Software modules for machine learning are advantageously distinguished by high speed, robustness, and flexible or universal applicability and usability. The quality of the segmentation may be continuously improved during operative use, as described herein.

According to a further independent aspect of the improved concept, an apparatus for the automatic localization of a structure is provided. The apparatus has a display device with a display surface and a computer unit configured to display on a display surface an individual image which maps an object with the structure. The apparatus has a gaze capture system configured to capture a gaze movement of a user of the apparatus and, on the basis thereof, to generate a gaze capture signal. The computer unit is configured, dependent upon the gaze capture signal, to identify at least one image point of the individual image, wherein the at least one image point at least partially maps the structure.

The gaze capture system may also be designated an eye tracker.

According to at least one embodiment of the apparatus, the apparatus has an imaging apparatus configured to image the object in order to generate the individual image.

The imaging apparatus may be an X-ray device, a computed tomography device, a magnetic resonance tomography device, or an ultrasonic device.

According to at least one embodiment, the computer unit is configured, based on the at least one image point, to segment the structure at least partially automatically.

According to at least one embodiment, the apparatus has a software module for machine learning, for example, a computer-readable storage medium, on which the software module is stored, wherein the software module has been trained according to a method for training a software module for machine learning according to the improved concept. The computer unit is configured to segment the structure by the software module at least partially automatically.

Further embodiments of the apparatus arise directly from the different embodiments of the computer-implemented method for the automatic localization of a structure according to the improved concept and from the different embodiments of a computer-implemented method for training a software module for machine learning according to the improved concept and, respectively, vice versa. In particular, the apparatus according to the improved concept may be configured or programmed to carry out such a method according to the improved concept or the apparatus carries out such a method.

According to a further independent aspect of the improved concept, a training apparatus for training a software module for machine learning is provided. The training apparatus has a display device with a display surface and a training computer unit which is configured to display on the display surface a training individual image which maps a training object with the training structure. The training apparatus has a gaze capture system which is configured to capture a gaze movement of a user of the training apparatus and, on the basis thereof, to generate a training signal. The training computer unit is configured to segment the training structure at least partially automatically based on the training signal. The training computer unit is configured to train the software module based on a result of the segmentation.

Further embodiments of the training apparatus arise directly from the different embodiments of the computer-implemented method for training a software module according to the improved concept.

According to a further independent aspect of the improved concept, a computer program with commands is provided. On execution of the computer program by an apparatus for the automatic localization of a structure according to the improved concept, in particular, by the computer unit of the apparatus, the commands cause the apparatus to carry out a method for the automatic localization of a structure according to the improved concept or a method for training a software module for machine learning according to the improved concept.

According to a further independent aspect of the improved concept, a computer-readable storage medium is provided on which a computer program in accordance with the improved concept is stored.

The features and combinations of features mentioned in the description above and the following features and combinations of features mentioned in the description of the drawings and/or shown in the drawings alone are usable not only in the respective combination given, but also in other combinations without departing from the scope of the disclosure. Embodiments and combinations of features may also be regarded as disclosed which do not have all the features of an originally formulated independent claim and/or which go beyond or deviate from the feature combinations disclosed in the references of the claims.

BRIEF DESCRIPTION OF THE DRAWINGS

The disclosure will now be described in greater detail by reference to actual exemplary embodiments and the associated schematic drawings. In the figures, the same or functionally equivalent elements may be given the same reference characters. The description of the same or functionally equivalent elements will, where relevant, not necessarily be repeated in relation to different drawings.

FIG. 3 depicts an example of an individual image with a structure.

FIG. 4 depicts an example of a further individual image with a structure.

FIG. 5 depicts a schematic representation of an example of a segmented structure.

DETAILED DESCRIPTION

Figure 1:
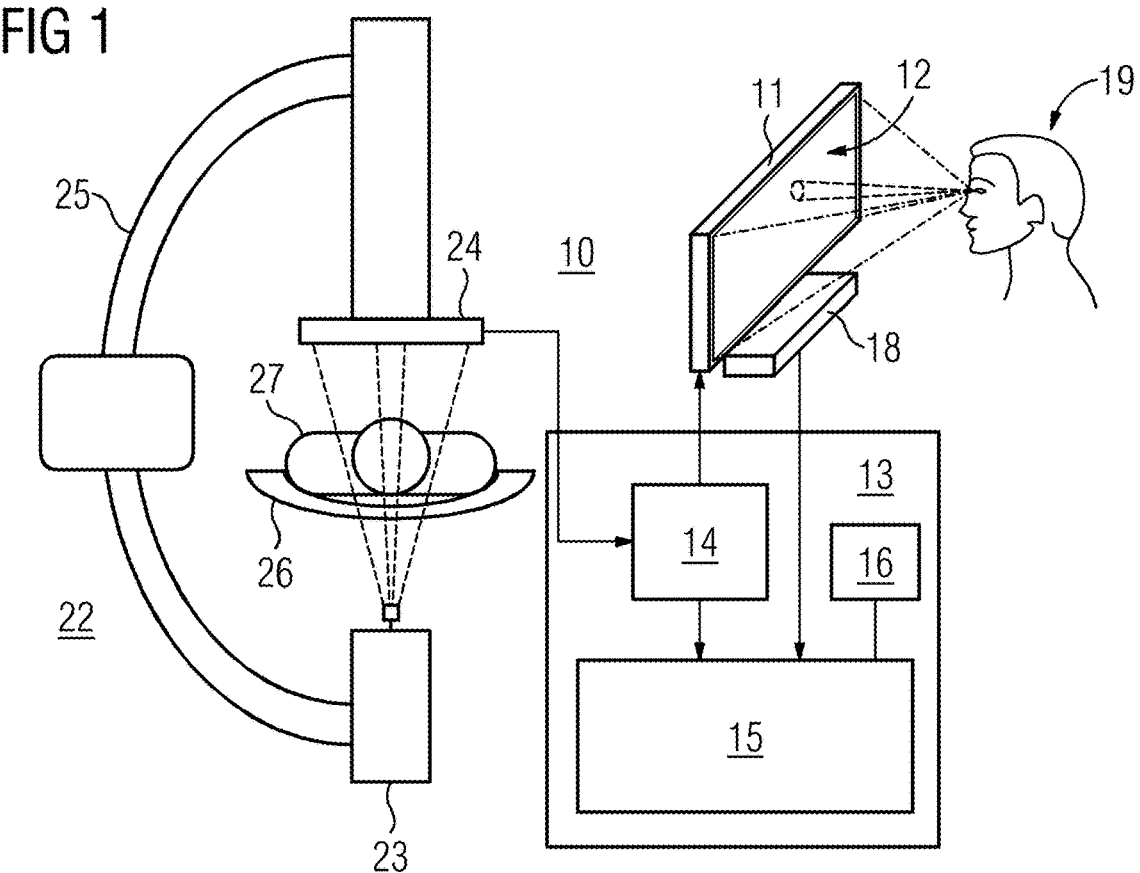
FIG. 1 depicts a schematic representation of an exemplary embodiment of an apparatus for the automatic localization of a structure according to the improved concept.

FIG. 1 depicts a schematic representation of an exemplary embodiment of an apparatus 10 for the automatic localization of a structure according to the improved concept.

The apparatus 10 has a computer unit 13 and a display device 11, for example, a monitor with a display surface 12.

The apparatus 10 has, for example, an imaging apparatus 22 which in the example of FIG. 1 is configured, by way of example, and not restrictively, as an X-ray device, (e.g., as a C-arm X-ray device).

The imaging apparatus 22 has, in this example, an X-ray source 23, an X-ray detector 24, and a support surface 26 on which an object 27, (e.g., a person), may be arranged. The X-ray source 23 emits X-ray rays which pass at least partially through the object 27 and are detected accordingly by the X-ray detector 24.

The X-ray detector 24 is connected to the computer unit 13, in particular to an X-ray image processor 14 of the computer unit 13 in order, based on the detected X-ray rays, to transfer detector signals to the X-ray image processor 14.

The X-ray image processor 14 may generate image data based on the detector signals and may display it as an individual image or as an image sequence of a plurality of successive individual images on the display surface 12.

In addition, the apparatus 10 includes an eye tracker 18 which is connected to an evaluation unit 15 of the computer unit 13. The eye tracker 18 may capture gaze movements of a user 19 who looks at the display surface 12, generate a gaze capture signal based on the captured gaze movements and transfer it to the evaluation unit 15.

The eye tracker 18 may be configured stationary and may be arranged, for example, on the display device 11. The eye tracker 18 may be configured as a mobile eye tracker, e.g., as an eye tracker mountable on the head (head-mounted eye tracker) configured to be worn by the user 19 on the head similarly to a pair of glasses.

In different embodiments, an output device mountable on the head, (also designated video goggles or a head-mounted display), may contain the display device 11, (e.g., the display surface 12), and the eye tracker 18. For example, the output device mountable on the head may be configured as so-called virtual reality goggles or augmented reality goggles.

The computer unit 13 has a storage medium with a software module 16 which contains a segmentation algorithm in the form of a corresponding source code. The segmentation algorithm may contain an artificial neural network or another software architecture based upon machine learning.

Figure 2:
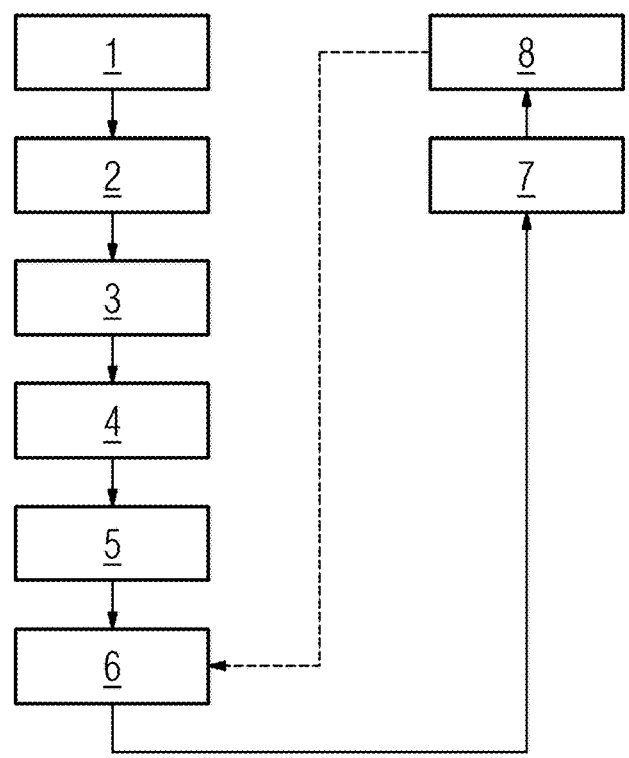
FIG. 2 depicts a flow diagram of an exemplary embodiment of an apparatus for the automatic localization of a structure according to the improved concept.

The functional method of the apparatus 10 will now be described in greater detail referring to FIG. 2. FIG. 2 is a flow diagram of an exemplary embodiment of a method for the automatic localization of a structure according to the improved concept.

In act 1 of the method, by the X-ray detector 24, the imaging apparatus 22 generates the detector signals and transfers them to the X-ray image processor 14.

In act 2, based on the detector signals, the X-ray image processor 14 generates one or more image data sets corresponding to one or more individual images and displays at least one individual image 17 on the display surface 12.

In act 3, while the individual image 17 is displayed on the display surface 12, the gaze movement of the user 19 is captured by the eye tracker 18. As described, on the basis thereof, the gaze capture signal is generated and is transferred to the evaluation unit 15.

In act 4 of the method, based on the gaze capture signal, the evaluation unit 15 determines one or more gaze positions of the user 19 on the display surface 12. In other words, the evaluation unit 15 determines which position or positions on the display surface 12, that is in particular, on the corresponding individual image 17 is observed or fixed by the user 19. For this purpose, on the basis, for example, of the gaze capture signal, the evaluation unit 15 may determine and process respective dwell durations of the gaze of the user 19 on the corresponding positions of the display surface 12.

Similarly, in act 4, the evaluation unit 15 receives the generated image data sets from the X-ray image processor 14 and allocates a corresponding region of the individual image 17, that is in particular, a region of image points of the individual image 17, to the determined gaze positions.

This is shown schematically in FIG. 3 where an individual image 17 is shown which represents, for example, a vessel system of a human that has been mapped by the imaging apparatus 22. Different gaze positions 20, 20', 20", 20'" on which the gaze of the user 19 was fixed for a certain time and which may accordingly be identified by the evaluation unit 15 based on the gaze capture signal and may be allocated to the corresponding image points of the individual image 17 are shown. A part of the vessel system, in particular, an individual vessel is the structure 9 which, for example, is to be segmented by the apparatus 10.

In the optional act 5 of the method, the acts described in relation to acts 2, 3 and 4 of the method may be repeated, wherein the individual image 17 may be displayed statically during this time. In this way, the number of gaze positions 20, 20', 20", 20'" and the identified points on the structure 9 in the individual image 17 may be increased accordingly.

Alternatively, or additionally, in act 5, the acts described in relation to acts 2 to 4 may be repeated for further individual images 17' of the image sequence. For example, the image sequence may be played out on the display surface 12 as a loop. For example, the user 19 may pause the playing-out in order to observe one of the individual images 17, 17' more exactly and, as described, to increase further the number of the identified gaze positions.

Shown in FIG. 4, by way of example, is a further individual image 17' of the image sequence. In act 5 of the method, in particular, further gaze positions 21, 21', 21", 21'" on the vessel 9 or the structure 9 in the further individual image 17' are identified, as described in relation to the individual image 17.

As is evident from a comparison of FIG. 3 and FIG. 4, the gaze positions 20, 20', 20", 20'" of the first individual image 17 are not necessarily identical with the further gaze positions 21, 21', 21", 21'" of the further individual image 17'. By this process, the quantity of information that may be accessed by the computer unit 13 for segmentation, may be increased. In particular, the computer unit 13 may assume with corresponding probability that all the gaze positions 20, 20', 20", 20', 21, 21', 21", 21" lie on the structure 9 or approximately on the structure 9.

In act 6 of the method, the evaluation unit 15 carries out the segmentation algorithm of the software module 16. In particular, the evaluation unit 15 uses the regions or image points of the individual images 17, 17' allocated to the gaze positions 20, 20', 20", 20'", 21, 21', 21", 21', for example, their positions to identify a coherent region which defines the structure 9 as completely as possible.

FIG. 5 depicts schematically a result of the segmentation of the structure 9. The result of the segmentation may be understood as a coherent or a non-coherent region of image points of the individual image or images 17, 17' which have been identified as belonging to the structure 9.

This information may be represented by the evaluation unit 15 or the X-ray image processor 14 on the display surface 12 in that, as indicated in FIG. 5, the result of the segmentation is visually emphasized.

In an optional act 7 of the method, the result of the segmentation may be verified or falsified, for example, by the user 19. Based on a result of the verification or falsification, the computer unit 13, (e.g., the evaluation unit 15), may adapt parameters of the segmentation algorithm in act 8, (e.g., weights of the neural network used therefor), in order to reduce errors and thereby further to train and optimize the, in particular, already pre-trained software module 16.

Alternatively, or additionally, in act 7, the evaluation unit 15 may undertake a comparison of the segmentation result with pre-determined reference data and carry out the adaptation of the parameters of the software module 16 based on a result of the comparison.

On a further segmentation by the method or the apparatus 10 according to the improved concept, the adapted software module 16 may then be used.

In other embodiments, the software module 16 is trained in advance, that is, before the operative use of the apparatus 10 or the software module 16.

As described, it is made possible according to the improved concept, to increase the level of automation for localization of structures on objects, in particular, in the context of the medical segmentation of anatomical objects and so to make manual interaction of a user at least partially superfluous.

Physicians and other users may have experience in recognizing structures in mappings from imaging processes, in particular, in image sequences as are used, for example, in the fluorescence-aided diagnosis, analysis, or treatment of patients. The experience of these persons may be used directly, by their gaze movement, for the automatic localization of structures according to the improved concept.

According to the improved concept, a gaze capture system or eye tracker is used, which in different embodiments continuously monitors the gaze of the user. By this process, the exact gaze position of the user may be followed. The eye tracker is synchronized with the computer unit and possibly with the imaging apparatus, so that the gaze direction or the gaze position of the user may be followed, including over a particular timespan, in particular, over a plurality of individual images of an image sequence.

In this way, the information may be extracted from the gaze movement. This gaze information may be integrated into the localization or segmentation algorithm to replace manual input via other input devices.

The gaze information may also facilitate landmark recognition. If, for example, a stenosis is present in an angiography image, it is probable that the gaze of the user contains information regarding the position of the stenosis. In some embodiments, the gaze information may also support a diagnosis because the gaze direction of the user may follow different patterns for different diagnosis results. For example, the gaze information for a coronary angiography in the case that a stenosis is present may differ from the case of a healthy vessel.

In different embodiments, the gaze capture signal or the gaze information may be used as an input variable for algorithms based upon machine learning, in order to carry out the localization or segmentation. In this way, the algorithm may use the additional information that is "stored" in the gaze movement of the user.

With different embodiments of the improved concept, for example, mouse clicks or other manual inputs which serve to define manually initialization points or regions for segmentation, may be replaced and so the level of automation in the segmentation may be increased decisively.

A further advantage of the improved concept is that the gaze information in the form of the gaze capture signal of the computer unit enables movements of the object, (e.g., due to breathing or organic movements), to be compensated for, because the user intuitively follows the contrasted vessels or organs with his gaze.

In comparison with conventional approaches to manual localization of structures, the improved concept does not require any interruption of the working processes of the user. Because the user normally uses the display surface in any case, the gaze movement may be captured by the user himself without further effort.

As a result of the increased level of automation, working processes, in particular, clinical working processes may be accelerated.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for an automatic localization of a structure, wherein an individual image which maps an object with the structure is displayed on a display surface, the method comprising:
   displaying an individual image on the display surface;
   capturing a gaze movement of a user by a gaze capture system while the individual image is displayed on the display surface;

generating a gaze capture signal based on the captured gaze movement;

identifying, by a computer, dependent upon the gaze capture signal, at least one image point of the individual image, wherein the at least one image point at least partially maps the structure;

displaying at least one additional individual image on the display surface, therein defining an image sequence comprising the individual image and the at least one additional individual image;

repeating the capturing, the generating, and the identifying for each additional individual image to provide at least one further image point for each additional individual image displayed in the image sequence, wherein each further image point at least partially maps the structure; and segmenting the structure at least partially automatically by the computer based on the identified at least one image point of the individual image and the at least one further image point for each additional individual image.

2. The computer-implemented method of claim 1, wherein, dependent upon the gaze capture signal, a gaze position is determined on the display surface by the computer, and
wherein the at least one image point is determined based on the gaze position.

3. The computer-implemented method of claim 1, wherein the displaying of the image sequence is repeated at least once, and
wherein the gaze movement is captured by the gaze capture system during a plurality of repetitions and the gaze capture signal is generated on the basis thereof.

4. The computer-implemented method of claim 1, wherein the displaying of the image sequence is paused,
wherein, during the pausing, the individual image or the at least one additional individual image is displayed, and
wherein the gaze movement is captured by the gaze capture system during the pausing and the gaze capture signal is generated on the basis thereof.

5. The computer-implemented method of claim 1, wherein a gaze movement of a further user is captured by the gaze capture system for the individual image or the at least one additional individual image,
wherein a further gaze capture signal is generated based on the captured gaze movement of the further user, and
wherein at least one further image point is identified by the computer dependent upon the further gaze capture signal.

6. The computer-implemented method of claim 1, wherein the object is mapped by an imaging apparatus in order to generate the individual image.

7. The computer-implemented method of claim 1, wherein the structure is an anatomical structure or a part of an anatomical object.

8. The computer-implemented method of claim 7, wherein the anatomical structure is an organ, an anatomical vessel, a tumor, or a part thereof.

9. The computer-implemented method of claim 1, further comprising:
checking a result of the segmenting of the structure; and
adapting parameters based on the result of the segmenting to optimize the computer-implemented method for the automatic localization of the structure.

10. The computer-implemented method of claim 9, wherein the checking is performed by the user.

11. The computer-implemented method of claim 9, wherein the checking is performed by the computer and comprises comparing the result with pre-determined reference data.

12. A computer-implemented method for training a software module for machine learning, the method comprising:
displaying, on a display surface, a training individual image which maps a training object with a training structure;
capturing a gaze movement of a user by a gaze capture system;
generating a training signal based on the captured gaze movement;
identifying, by a training computer, at least one image point dependent on the generated training signal, wherein the at least one image point at least partially maps the training structure;
displaying at least one additional training image on the display surface, therein defining an image sequence comprising the training individual image and the at least one additional training image;
repeating the capturing, the generating, and the identifying for each additional training image to provide at least one further image point for each additional training image displayed in the image sequence, wherein each further image point at least partially maps the training structure; and
segmenting, by the training computer, the training structure at least partially automatically based on the at least one image point and the at least one further image point for each additional training image; and
training the software module based on a result of the segmentation by the training computer.

13. The computer-implemented method of claim 12, wherein the training structure is at least partially automatically segmented by the software module for machine learning.

14. An apparatus for an automatic localization of a structure, the apparatus comprising:
a computer;
a display device having a display surface configured to display an image sequence comprising a plurality of individual images, wherein individual image of the plurality of individual images maps an object with the structure on the display surface;
a gaze capture system configured to capture a gaze movement of a user of the apparatus and generate a gaze capture signal based on the captured gaze movement for each individual image of the plurality of individual images displayed in the image sequence; and
a software module for machine learning,
wherein the computer is configured, dependent upon a respective gaze capture signal, to identify at least one image point of the respective individual image of the plurality of individual images in the image sequence, wherein each at least one image point of the respective individual image at least partially maps the structure,
wherein the display device is further configured to display at least one additional image on the display surface, therein defining an image sequence comprising the individual image and the at least one additional image,
wherein the gaze capture system and computer are further configured to repeat, for each additional at least one image, the capture of the gaze movement, the generation of the gaze capture signal, and the identification of at least one further image point of the respective at least one additional image, wherein the at least one further image point at least partially maps the structure, wherein the computer is further configured, based on the identified at least one image point of the individual image and the at least one further image point for each additional individual image, to segment the structure at least partially automatically, and wherein the software module is configured to be trained based on a result of the segmentation by the computer.

* * * * *